United States Patent [19]

Vreeke et al.

[11] Patent Number: 5,534,132
[45] Date of Patent: Jul. 9, 1996

[54] ELECTRODE AND METHOD FOR THE DETECTION OF AN AFFINITY REACTION

[76] Inventors: Mark Vreeke, 14603 Cedar Point, Houston, Tex. 77070; Patrick Rocca, 91, Chemin de Cléres, 76130 Mont-Saint-Aignan, France

[21] Appl. No.: 434,782

[22] Filed: May 4, 1995

[51] Int. Cl.$^6$ .................................................. G01N 27/26
[52] U.S. Cl. ........................ 205/777.5; 204/403; 204/418; 435/817; 435/4; 435/7.1; 435/7.5; 435/25; 435/287.2; 435/287.9
[58] Field of Search ........................ 205/777.5; 204/403, 204/418; 435/817, 288, 291, 4, 7.1, 7.5, 25

[56] References Cited

U.S. PATENT DOCUMENTS

| | | | |
|---|---|---|---|
| 4,233,144 | 11/1980 | Pace et al. | 204/195 |
| 4,886,625 | 12/1989 | Albarella et al. | 252/500 |
| 5,126,034 | 6/1992 | Carter et al. | 204/403 |
| 5,147,781 | 9/1992 | Rishpon et al. | 435/7.4 |
| 5,200,051 | 4/1993 | Cozzette et al. | 204/403 |
| 5,225,516 | 7/1993 | Abuknesha | 528/176 |
| 5,264,105 | 11/1993 | Gregg et al. | 204/403 |
| 5,320,725 | 6/1994 | Gregg et al. | 204/153.12 |
| 5,346,832 | 9/1994 | Aizawa et al. | 436/518 |
| 5,352,574 | 10/1994 | Guiseppi-Elie | 435/4 |
| 5,391,272 | 2/1995 | O'Daly et al. | 204/153.12 |

OTHER PUBLICATIONS

Heut et al. Automatic apparatus for heterogeneous enzyme immunoassays based on electrocatalytic detection of the enzyme and electrochemical regeneration of the solid phase Anal. Chim. Acta vol. 272 (1993) pp. 205–212.

Gleria et al. Homogeneous Ferrocene–Mediated Amperometric Immunoassay, *Anal. Chem.* vol. 58 (1986) pp. 1203–1205.

Masuo Aizawa Enzyme–Linked Immunosorbent Assays Using Oxygen–Sensing Electrode, in Electrochemical Sensors in Immunological Analysis, (1987) pp. 269–278.

Hadas et al. A Rapid and Sensitive Heterogeneous Immunoelectrochemical Assay Using Disposable Electrode, *J. of Immunoassay*, vol. 13 (1992) pp. 231–252.

Bourdillon et al. A Fully Active Monolayer Enzyme Electrode Derivatized by Antigen–Antibody Attachment, *J. Am. Chem. Soc.* vol. 115 (1993) pp. 12264–122669.

Xu et al. Heterogeneous Enzyme Immunoassay of Alpha–Fetoprotein in Maternal Serum by Flow–Injection Amperometric Detection of 4–Aminophenol, *Clin. Chem.* vol. 36 (1990) pp. 1941–1944.

Gil et al. Competitive Heterogeneous Enzyme Immunoassay for Theophylline by Flow–Injection Analysis with Electrochemical Detection of p–Aminophenol, *Clin. Chem.* vol. 36 (1990) pp. 662–665.

Duan et al. Separation–Free Sandwich Enzyme Immunoassay Using Microporous Gold Electrodes and Self–Assembled Monolayer/Immobilized Capture Antibodies, *Anal. Chem.* vol. 66 (1994) pp. 1369–1377.

Ohara et al. Glucose Electrodes Based on Cross–Linked [Os(bpy)2Cl]+/2+ Complexes Poly(1–vinylimidazole) Films, *Anal. Chem.* vol. 65 (1993) pp. 3512–3517.

*Primary Examiner*—Bruce F. Bell

[57] ABSTRACT

An amperometric biosensor for the detection of an affinity reaction is described. The sensor includes an electrode having on its testing surface a hydrogel in which a selective binding unit and redox species are immobilized.

15 Claims, 11 Drawing Sheets

ELECTRODE AND METHOD FOR THE DETECTION OF AN AFFINITY REACTION

BACKGROUND—FIELD OF THE INVENTION

This invention relates to an amperometric biosensor or electrode for the detection of an affinity reaction. It includes a method for quantitative or qualitative measurement of the affinity reaction. More specifically, this invention is drawn to an electrode having a surface substantially covered with a three-dimensional polymer hydrogel network in which a selective binding unit or its complement is immobilized along with a redox species.

BACKGROUND—DISCUSSION OF PRIOR ART

Affinity sensors are characterized by the detection of the coupling reaction between selective binding unit (SBU), e.g. avidin,[1] antibody, single stranded DNA, lectin,[2] and host artificial molecular recognition species, and its complementary component, e.g. biotin, antigen, complementary single stranded DNA, sugar sequence, and guest target compound. Affinity sensors are designed so that binding of SBU and complement takes place on the transducer surface making them implicitly heterogeneous in nature. The transducer converts the binding event into a measurable response. The sensors can be divided into two categories: non-labeled and labeled. Non-labeled affinity sensors directly detect the affinity complex by measuring physical changes at the transducer induced by the formation of the complex. In contrast, labeled affinity sensors incorporate a sensitively detectable label, and the affinity complex is thus determined through measurement of the label.

[1] Avidin is a ~60kD protein with 4 bindings sites highly selective for biotin
[2] Lectins are proteins capable of binding to cell surfaces by targeting specific carbohydrate groups. They are thought to be involved in cellular recognition.

Typically, detection of the binding event is not a direct measurement, and labeling of either SBU or complement is used to aid in signaling the binding event. Enzyme labels are particularly useful in providing signal amplification, and by their incorporation a higher sensitivity is achieved. Since enzyme electrodes effectively coupled redox enzymes with amperometric detection, there was a natural progression to coupling enzyme-labeled affinity reactions and amperometric detection. Heinemann et al. [Xu, Y.; Halsall, H. B. Heineman, W. R. *Clin. Chem.* 1990, 36, 1941–4.; Gil, E. P.; Tang, H. T.; Halsall, H. B.; Heineman, W. R.; Misiego, A. S. *Clin. Chem.* 1990, 36, 6625.; Xu, Y.; Halsall, H. B.; Heineman, W. R. *J. Pharm. Biomed. Anal.* 1989, 7, 1301–11.] pioneered the use of alkaline phosphatase-antibody conjugates to perform sandwich immunoassays in which aminophenyl phosphate is used as a substrate (in place of nitrophenyl phosphate), and the aminophenol product is detected anodically with an FIA system. Aizawa et al. [Aizawa, M.. In *Electrochemical Sensors in Immunological Analysis*; Ngo, T. T., Ed.; Plenum Press:N.Y., 1987; 269–78.] devised a host of sensors with a classical Clark-type $O_2$ electrode as the base sensor and catalase as the enzyme label. Catalase was used to decompose $H_2O_2$ to $O_2$ and $H_2O$. When the enzyme label is immobilized at the sensor surface by an affinity reaction, an increase in $O_2$ signal is observed in a $H_2O_2$ solution. Rishpon, [Hadas, E.; Soussan, L.; Margalit, I. R.; Farkash, A.; Rishpon, J. *Journal of Immunoassay* 1992, 13, 231–52.] Bourdillon, [Huet, D.; Bourdillon, C. *Anal Chim. Acta* 1993, 272, 205–212.; Bourdillon, C.; Demaille, C.; Gueris, J.; Moiroux, J.; Savéant, J-M. *J. Am. Chem. Soc.* 1993, 115, 12264–69.] and others [Gleria, K. D.; Hill, H. A. O.; McNeil, C. J.; Green, M. J. *Anal. Chem.* 1986, 58, 1203–5.; Robinson, G. A.; Cole, V. M.; Rattle, S. J.; Forrest, G. C. *Biosensors*, 1986, 2, 45–7.] have developed electrode based affinity sensors using enzyme labels and the immobilization of an affinity component at the electrode surface. Although, excellent sensitivities were obtained, these assays were hampered by the need to wash the working electrode and change incubating and testing solutions. The problem lay with the difficulty in distinguishing enzyme catalyzed reaction in bulk solution from surface associated reactions. This required the electrodes to be washed and the incubation solutions changed.

A goal of affinity sensors has been the development of non-separation methods where wash steps (a source of irreproducibility) are not necessary. In a recent article Duan and Meyerhoff proposed a scheme, where the substrate which is converted into electroactive product, is brought into the cell from behind the electrode. [Duan, C.; Meyerhoff, M. E. *Anal. Chem.* 1994, 66,136;9–1377.] This allowed for measurement of the binding reaction without the usual washing steps. However, a specially designed cell and electrodes were necessary.

SUMMARY OF THE INVENTION

The disclosed invention demonstrates a fast, compact, inexpensive, and separation free amperometric affinity sensor. The sensor is constructed by immobilizing a selective binding unit (SBU) into a three dimensional electron conducting redox hydrogel (enzyme "wiring") on a vitreous carbon electrode. The SBU provides the electrode affinity for the SBU's complementary component. Incubation of the affinity sensor with its complementary component leads to selective uptake of the complement from the solution. If the complement is first labeled with a redox enzyme, incubation leads to binding of the redox enzyme to the "wiring" gel on the electrode. The selective binding agent serves to bring a redox enzyme labeled complement into the hydrogel. In this way the electrode can then generate an amperometric response through electrocatalytic reduction/oxidation of enzyme substrate and transduction of the redox enzyme's activity through the hydrogel to the electrode.

The affinity sensors described operate by "wiring" an enzyme covalently bound to the complement. When a redox enzyme labeled complement contacts the redox gel to which the SBU is covalently bound, the binding event immobilizes the redox enzyme. When substrate for the redox enzyme is present, an electrocatalytic current flows.

In the first example, avidin immobilized in the "wiring" redox hydrogel assayed peroxidase labeled biotin. When biotin label peroxidase was incubated with the affinity electrode, the avidin bound the biotin forming an affinity complex. This also immobilized the peroxidase attached to the biotin. When the peroxidase substrate was present a current related to the amount of bound peroxidase was generated.

Using a competitive process the affinity sensor could detect SBU that was free in the incubation solution, i.e. an unknown concentration of SBU (avidin), free in the solution, was allowed to compete with electrode-immobilized SBU for a limited number of enzyme labeled complement molecules (peroxidase labeled biotin). The current resulting from the electrocatalytic reduction of $H_2O_2$ was higher when fewer complement SBUs were present in the solution.

In a similar assay the complement to the SBU (biotin) was assayed by allowing a fixed number of labeled complement molecules to compete with an unknown concentration of complement that was not redox-enzyme labeled for the limited number of SBUs immobilized at the electrode. The current was inversely related to the amount of unlabeled complement.

DESCRIPTION OF THE INVENTION

Figure 1:
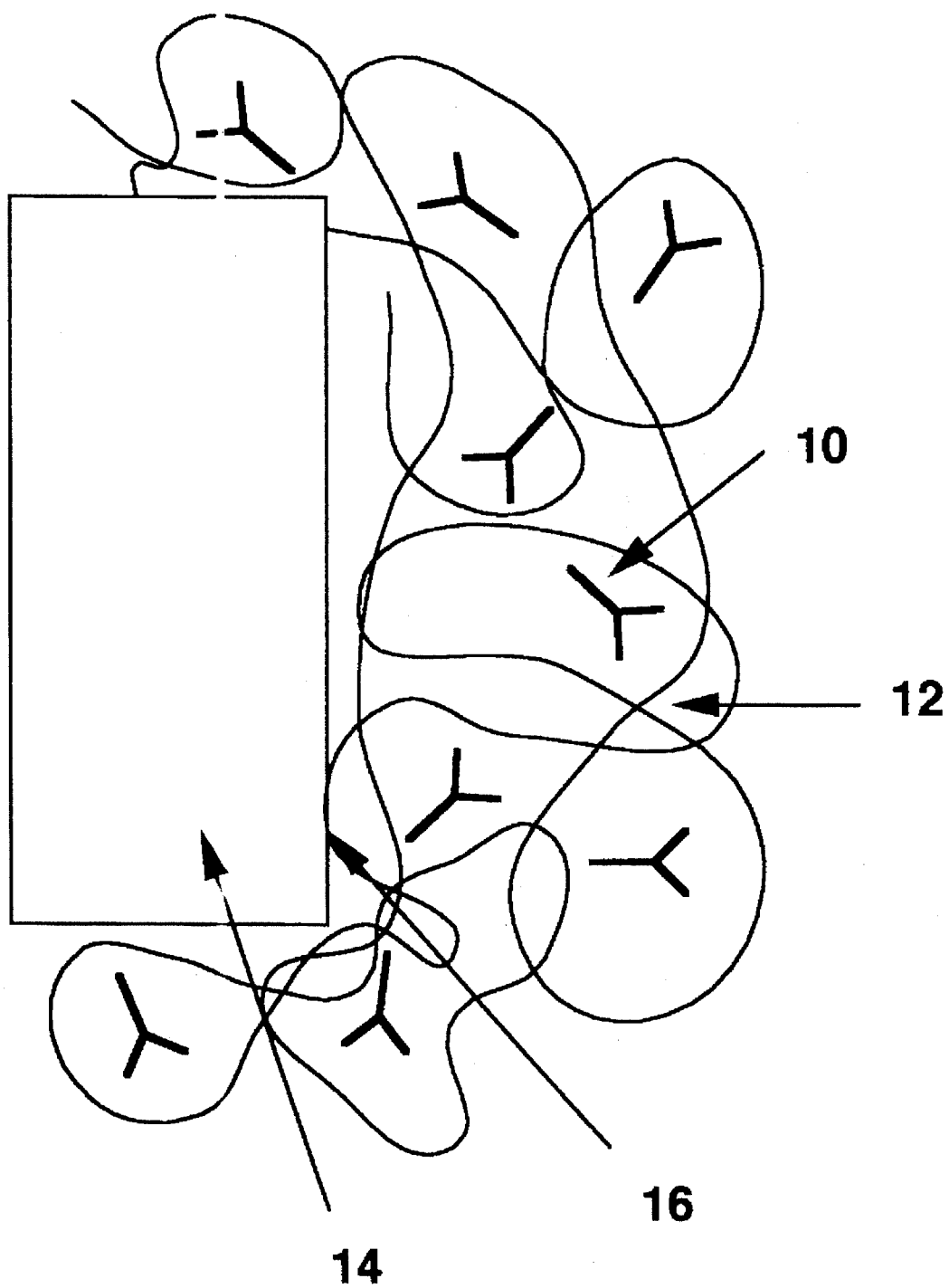
FIG. 1. Pictorial diagram of the electrode sensor

As shown in FIG. 1, a biosensor of the present invention includes an electrode 14 having a testing surface 16. The surface 16 is substantially covered with a three-dimensional hydrogel 12 in which a SBU 10 is immobilized, preferably chemically bound, to the redox polymer. The electrode 14 may be formed of any material known for the manufacture of biosensing electrodes. Preferably the electrode is formed of a solid material, e.g., gold or glassy carbon. Additional suitable electrode materials include graphite, platinum, palladium, tin oxide, and conducting organic salts.

The three-dimensional hydrogel includes at least two components. At least one of these components comprises a redox compound, and at least one other component comprises a SBU. The three-dimensional molecular structure has multiple redox centers and has the SBU immobilized within.

The term "immobilized" is meant to describe a SBU which is retained within the redox polymer network and does not freely diffuse away. The SBU may be entrapped, but is preferably chemically bound, and more preferably covalently bonded to the redox polymer.

The SBU may be any of the biological reagents that are able to form an affinity complex including the biotin with avidin complex, antibody with antigen complex, single stranded DNA with the corresponding opposite strand, and lectin with specific sugar sequence. Alternatively, the complex could be any .of the artificial host/guest complexes.

As used here the term "affinity complex" refers to the joint structure of the SBU and its corresponding complement. These complexes include those where the complexations are reversible and irreversible.

The term "redox compound" is used herein to mean a compound that can be oxidized and reduced. The redox compound may have one or more functions that are reducible and oxiidizable. Further, the term "redox compound" means a compound which contains one or more redox centers. "Redox center" meaning a chemical function that accepts and transfers electrons.

The redox compounds, or redox centers contained within compounds useful in this invention may be organic or inorganic. Transition metal complexes with organic ligands such as, bipyridine and the like, are preferred as redox centers because of their chemical stability and various oxidation states and their facial electron transfer kinetics. Examples of such complexes include polypyridine complexes of di or trivalent osmium ions. However, a number of organic redox centers may also be employed. Various derivatives of viologen (N,N'-bis alkyl-4,4'-bipyridine) constitute typical examples of this class. A number of preferred crosslinkable compounds containing redox active centers are known. Some of these compounds require only the addition of SBU to form 3-dimensional crosslinked films, i.e., the SBU is the only required crosslinking agent. Other redox compounds do not directly react with the chemical functions present on the SBU and thus require a separate crosslinking agent to form the 3-dimensional network.

Figure 2:
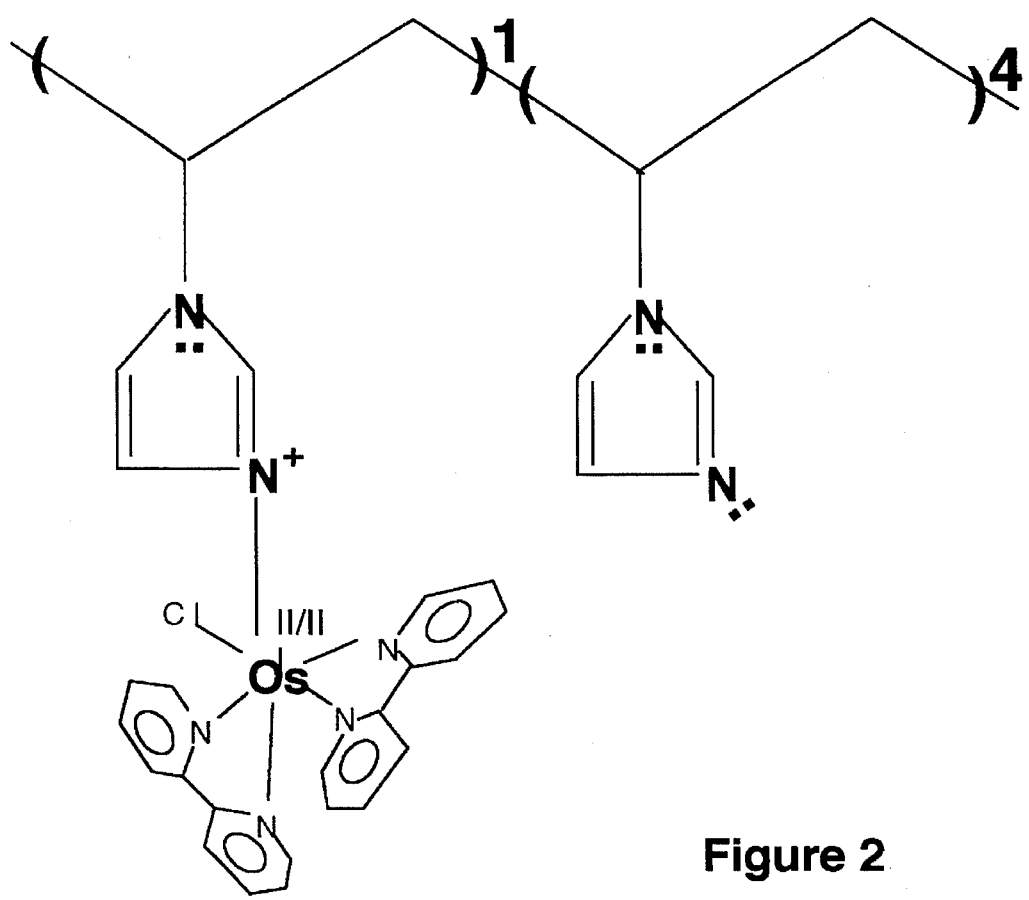
FIG. 2. Structure of the PVI-Os polymer

A preferred redox polymer complex for use in the present invention is PVI-Os shown in FIG. 2. To prepare PVI-Os, poly(vinylimdazole) is complexed with [osmium bis(2,2'-bipyridine) dichloride] to yield the polymer.

Figure 3:
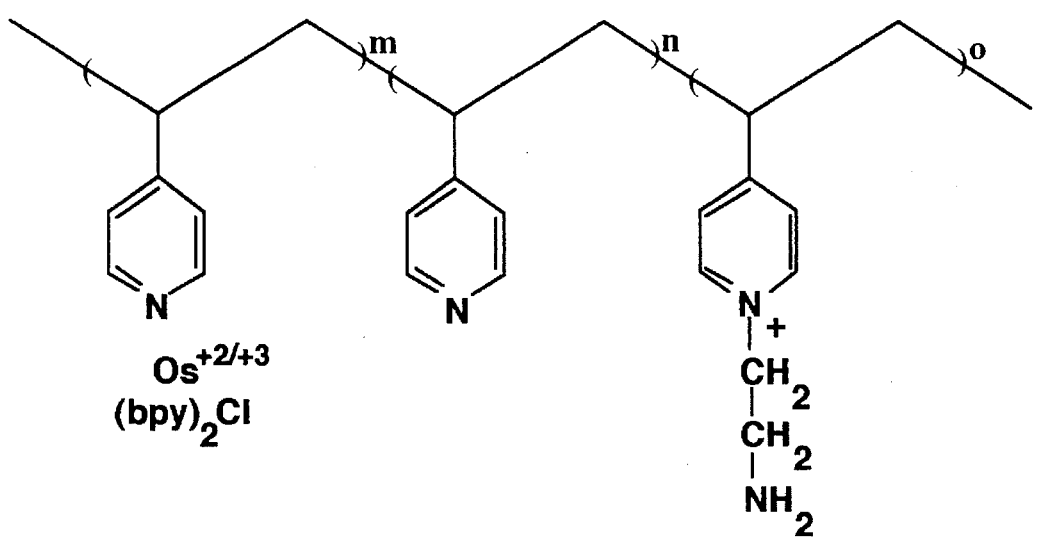
FIG. 3. Structure of the PVP-Os-$NH_2$ polymer

Other redox polymers useful in this invention also include derivatives of poly(vinylpyridine) (PVP) complexed with $[Os(bpy)2Cl]^{+/2+}$ to yield the polymer abbreviated PVP-Os. This polymer (PVP-Os) is then quaternized with bromoethylamine hydroibromide to form a very hydrophilic, crosslinkable redox polymer containing pendant ethylamine groups (PVP-Os-$NH_3$) as shown in FIG. 3.

In a preferred embodiment, the three-dimensional redox polymer network includes a SBU, a cross-linking agent, and a cross-linkable compound capable of reacting with the cross-linking agent and the SBU. Either the cross-linkable compound or the cross-linking agent, or both, contain at least one but preferably multiple redox centers.

Preferred cross-linking agents are water soluble compounds that react under conditions where the SBUs are stable, that is, in aqueous solutions, approximately at pH 3–9 and at 0°–50° C. Included in this category of cross-linking agents are multi-functional epoxides such as polyetheylene glycol diglycidyl ether (PEGDGE), carbodiimides, and di and poly aldehydes, and N-hydroxysuccinimid esters. These reagents may react with one or more type of functions including amides, alcohols, thiols and carboxylic acids which may be present on the surface of the SBU and which may also be included in the structure of the redox compound.

Preferred crosslinkable compounds are hydrophylic, containing chemical groups such as alcohols, carboxylic, acids, amines, sulfonates, phosphates, and phosphonates. Such groups tend to promote the solubility of the components in water which facilitates contact with the water soluble SBUs. Such groups may also improve the stability of the immobilized SBU against denaturation.

Some care must be taken in the cross-linking process to ensure that some fraction of the immobilized SBU's retain their affinity for their appropriate conjugate, and that the resulting hydrogel polymer network be flexible enough to allow binding by a labeled conjugate.

To form the inventive electrodes, the components of the three-dimensional redox polymer network arc; mixed together under appropriate conditions such that a chemical reaction takes place resulting in the formation of a three-dimensional redox polymer having SBU bound within a three-dimensional hydrogel network.

Mixture of SBU and the various polymer components in a common solution is followed by the application of the solution to an electrode surface. Various application methods may be used, including the addition of drops of the solution onto the electrode surface, dip coating, spin coating, or spraying the solution onto tile electrode surface. The application step is followed by a curing or setting step, involving drying of the electrode. Alternatively, the process may involve the addition of the SBU and polymer components in separate solutions to the surface of the electrode, mixing, and then curing or setting.

When such materials are coated onto an electrode surface, the three-dimensional molecular structure which results allows SBU to complex with its complement. When the complement is labeled with a redox enzyme the complex formed by complement binding the immobilized SBU provides electrical contact between the surface of the electrode and the labeling redox enzyme.

Figure 4:
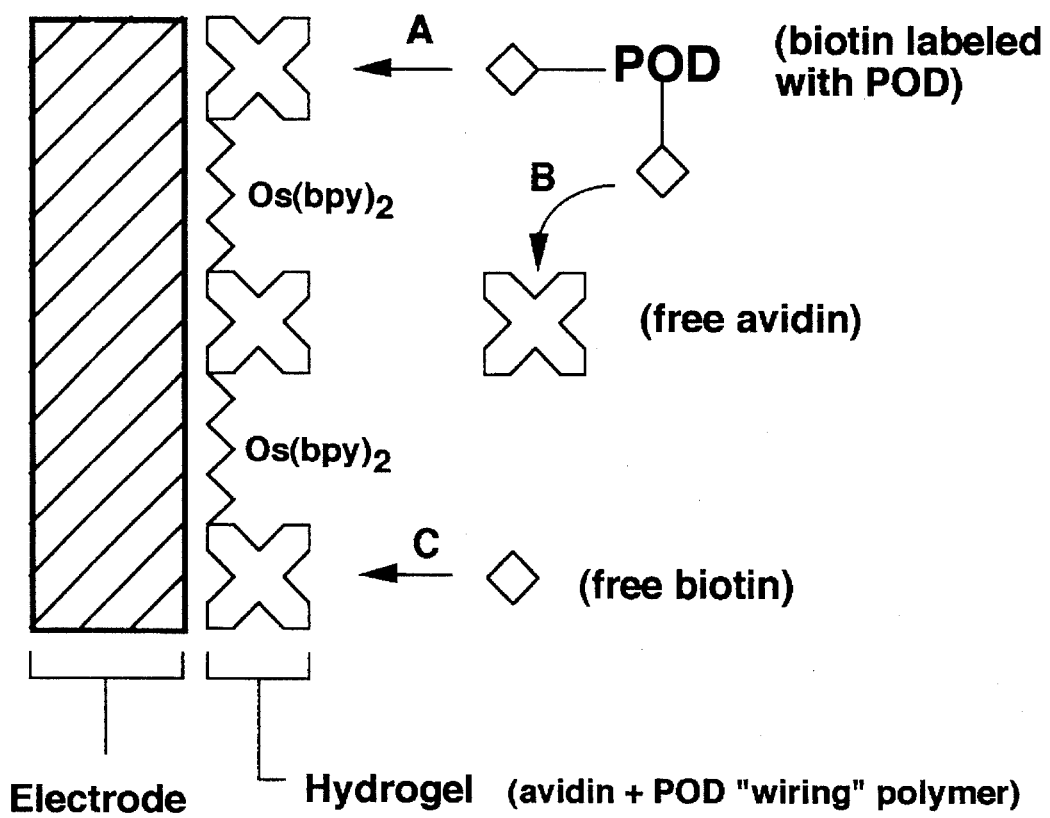
FIG. 4. Pictorial diagram showing the, binding occurring at the electrode and two possible competitive assays.
Figure 5:
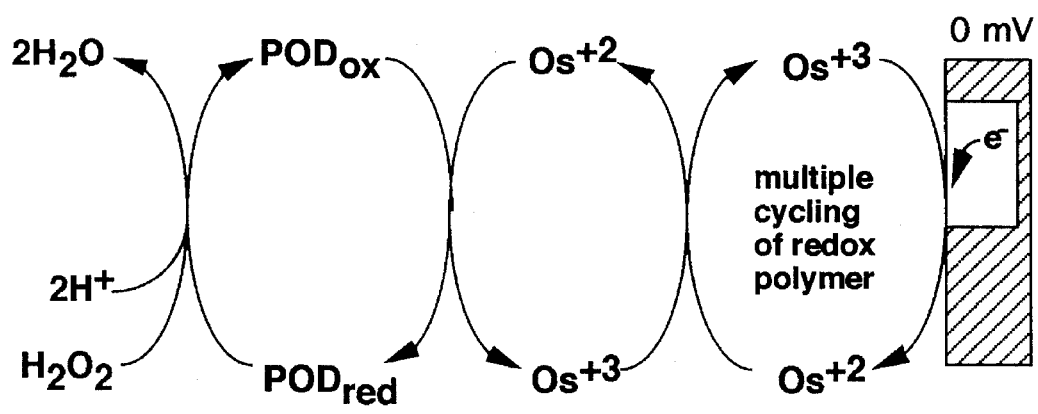
FIG. 5. Catalytic cycles occurring at the electrode if a labeling peroxidase enzyme is selectively bound FIG. 6. Response of the bound peroxidase to $H_2O_2$ concentration FIG. 7. Sensor response to the amount of bound biotinylated peroxidase FIG. 8. Time response of the affinity sensor for binding FIG. 9. Competitive assay with free biotin FIG. 10. Competitive assay with free avidin FIG. 11. Reversible sensor response with antibody to biotin as the selective binding unit.

In the method of the present invention, the inventive electrode is used to directly detect redox enzyme labeled complement in a test sample. This is pictorially described in FIG. 4 path A for the avidin biotin affinity complex. Here the SBU (avidin) is immobilized at the electrode in the hydrogel and the conjugate biotin is labeled with a peroxidase redox enzyme. In this method, the affinity sensor is incubated in a solution containing redox labeled complement (B-POD). Binding of the complement selectively immobilizes redox enzyme in the hydrogel. Addition of redox enzyme substrate generates an electrical signal detectable at the electrode. In the case of peroxidase labels electrons generated at the electrode are relayed to the peroxidase enzyme through the hydrogel network to which the peroxidase is selectively bound by SBU. As shown in FIG. 5, electrons are relayed to the peroxidase enzyme which is electroreduced at potentials negative of 0.35 V (Ag/AgCl), generally measurement is at +100 mV (Ag/AgCl). In the presence of the enzyme's substrate $H_2O_2$ in the test sample, the electrons are then transferred from the reduced peroxidase to hydrogen peroxide generating the flow of an electrical current. This current is a function of the concentration of biotinylated peroxidase immobilized at the electrode by the SBU.

The inventive electrode can detect SBU by a competitive process, i.e. an unknown concentration of SBU, free in the solution, is allowed to compete with electrode-immobilized SBU for a limited number of enzyme labeled complement molecules. This process is pictorially represented in FIG. 4 path B again for the avidin biotin affinity complex. Here SBU (avidin) free in solution competes with hydrogel immobilized SBU for the limited peroxidase labeled complement. The free SBU effectively prevents the complement from complexing with the SBU in the wiring hydrogel. The current resulting from the electrocatalytic reduction of $H_2O_2$ is higher when fewer complement SBUs are present in the solution.

In a similar assay the complement to the SBU is assayed by allowing a fixed number of labeled complement molecules to compete with an unknown concentration of complement that is not redox-enzyme labeled for the limited number of SBUs immobilized at the electrode. The process is pictorially presented in FIG. 4 path C again for the biotin avidin system. The current generated from oxidation/reduction of enzyme substrate is inversely related to the amount of unlabeled complement.

"Incubation" refers to the necessary step of allowing the SBU and its complement time to selectively bind forming the affinity complex.

"Electrical contact" is defined as the situation where current will flow in the external circuit as a result of oxidation or reduction reaction in one or more layers of the sensor.

OPERATION OF INVENTION

The following examples are designed to illustrate certain aspects of the present invention. The examples are not intended to be comprehensive of all features and all embodiment of the present invention, and should not be construed as limiting the claims presented herein.

EXAMPLE 1

Production of Biotin Affinity Electrodes

Rotating disk electrodes were made of vitreous carbon rods, one centimeter in length, three millimeters in diameter. The disk electrodes were press-fitted into one end of a Teflon sleeve. The opposite end of the sleeve contained a press-fitted stainless steel rod threaded to match an electrode rotator. Electrical contact between the vitreous carbon and stainless steel rods was made with a silver epoxy EPO-TEK H2OE (Epoxy Technology, Inc., Billerica, Mass.). The electrodes were polished successively with 5 µm, 1 µm, and 0.3 µm alumina with thorough sonication (3–6 min.) after each polishing step.

Bovine serum albumin fraction V (BSA) (#A-3059), avidin (#A-9275), biotin (#B-4501), horseradish peroxidase (HRP) (#P-6782), and biotin labeled horseradish peroxidase with 2.6 biotins per HRP (B-HRP) (#P-9568) were purchased from Sigma. Sigma states the activity of HRP as 280 units/mg and of B-HRP as 250 units/mg, where one unit of HRP or B-HRP forms 1.0 mg of purpurogallin from pyrogallol in 20 sec. at pH 6.0 at 20° C. Poly(ethylene glycol 400 diglycidyl ether) (PEGDGE), tech. grade was purchased from Polysciences (#08210). PEGDGE is used as a cross-linker to immobilize the components forming the hydrogel. A 30% hydrogen peroxide solution was purchased from Aldrich, and its concentration was verified through measuring its density. The radox polymer poly(1-vinylimidazole) modified with osmium bipyridine redox centers (PVI-Os) was synthesized as previously described (FIG. 2) [Ohara, T. J.; Rajagopalan, R.; Heller, A. *Anal. Chem.* 1993, 65, 3512–3517.]. The polymer had approximately 20% of the imidazole rings complexed to osmium radox centers, however, the exact ratio is not important so long as enough osmium sites are, present to "wire" the redox enzymes.

The best films were made by mixing 6 mg/mL avidin, 10 mg/mL PVI-Os, and 2.5 mg/mL PEGDGE in a 1:1:1 ratio. 1 µL of the 1:1:1 solution was loaded on a 3 mm diameter glassy carbon electrode. Films varying in their avidin content could be made by increasing the avidin/radox polymer ratio, while keeping the amount of PVI-Os and PEGDGE fixed. After drying, the films were cured for a minimum of 24 hours at room temperature before use. The cross-linking of PVI-Os and Avidin was accomplished by the reaction of the diepoxy (PEGDGE) with primary amines on the avidin and ring nitrogens on the PVI backbone.

EXAMPLE 2

Operation of Avidin Affinity Electrodes

Modified Dulbecco's buffer (PBS) pH 7.4 was used as the incubation and electrolytic solution. The electrochemical measurements were performed using a standard three electrode cell with a platinum wire counter electrode and an Ag/AgCl Bioanalytical Systems reference electrode, relative to the potential of which all potentials are reported, the working electrode being the affinity sensor. Either a Bioanalytical Systems Model CV-1B or an EG & G potentiostat/galvanostat Model 173 was used to operate the electrodes. The rotator was a Pine Instruments AFMSRX with an ACMDI 1906C shaft. The volume of the cell was 10 mL. It contained, in all experiments, 5 mL of the test solution.

The electrodes were rotated at 1000 RPM to enhance mass transfer and were poised at +100 mV vs Ag/AgCl. At this potential the background current, possibly resulting from $O_2$ reduction, was less than 10 nA, i.e. below $10^{-9}$ A $cm^{-2}$, while $H_2O_2$ was rapidly reduced by wired peroxidase. The electrodes were conditioned by rotation at 1000 RPM in PBS for 10 min., whereby any loosely bound avidin was removed. The binding of B-HRP to PVI-Os-avidin modified electrodes was observed at 25° C. $H_2O_2$, B-HRP, free biotin, or free avidin were added as aliquots of concentrated stock solutions, so as to hold the 5 mL volume of the solution reasonably constant. Once an electrode was immersed in a solution it was not allowed to dry.

Figure 6:
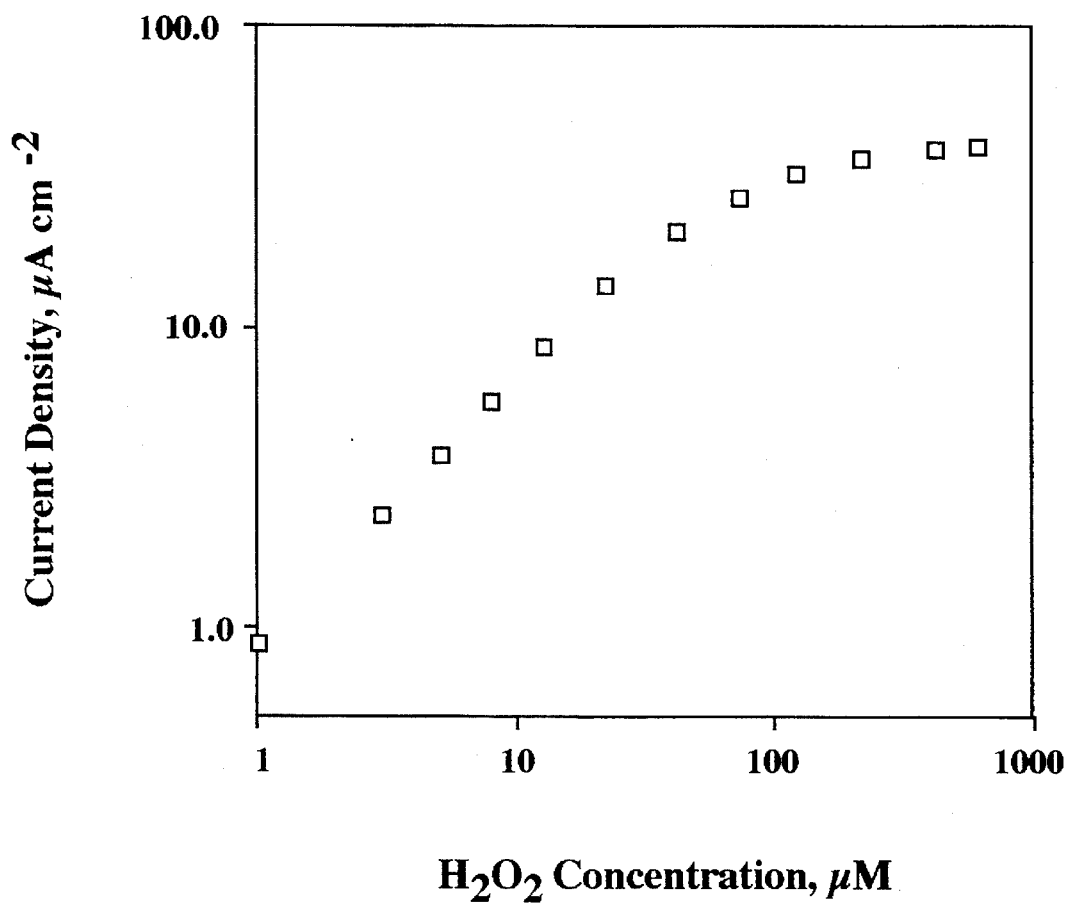

FIG. 6 shows the variation of the current density with $H_2O_2$ concentration, resulting from the electrocatalytic reduction of $H_2O_2$ to water, on a vitreous carbon electrode modified with 86 µg/cm2 hydrogel formed of 3.3 µg PVI-Os, 2.0 µg avidin, and 0.83 µg PEGDGE after incubation with 1 µg/ml B-POD for 20 minutes. The conditions were 5 mL PBS, 1000 RPM, and 100 mV AgAgCl. The current density increased linearly from 1 µM to 50 µM $H_2O_2$, reaching a plateau of 40 µA/cm$^2$ at a hydrogen peroxide concentration near 200 µM. At 100 µM hydrogen peroxide concentration the current density was already close to its maximum.

Figure 7:
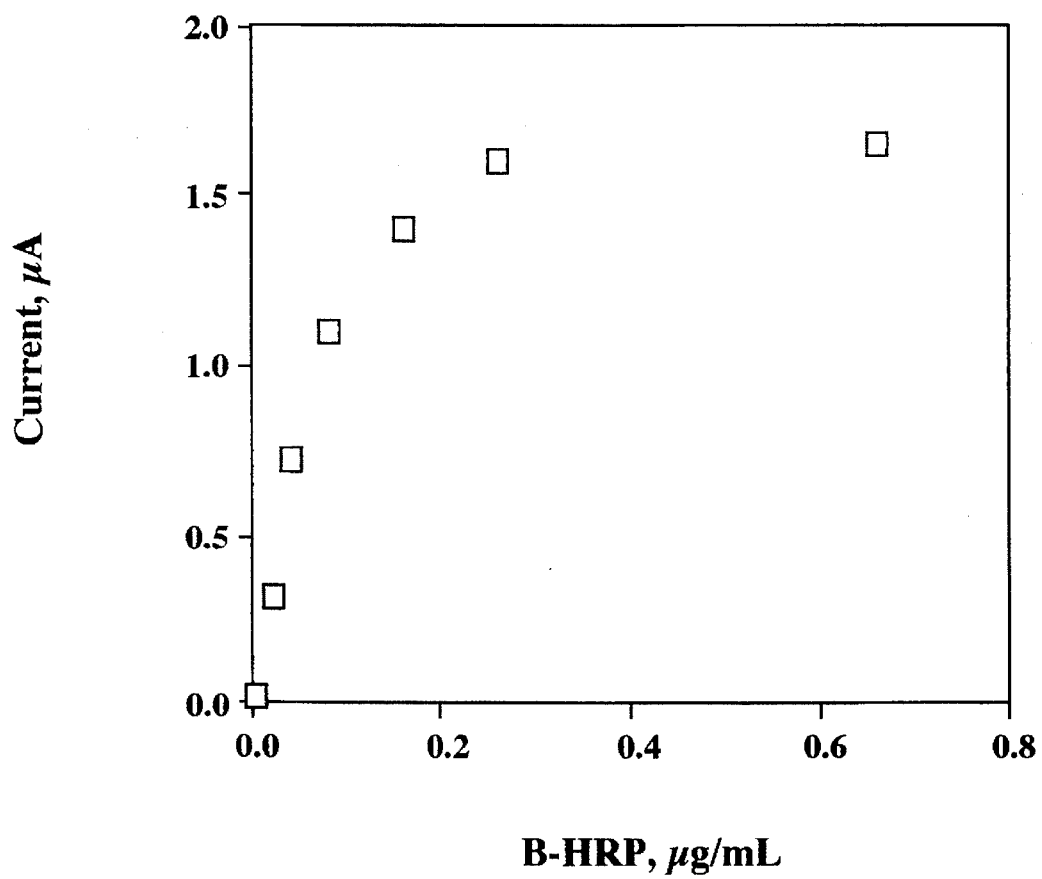

FIG. 7 shows the dependence of the $H_2O_2$ electroreduction current on a PVI-Os wire- avidin modified electrode (3.3 µg PVI-Os, 2.0 µg avidin, and 0.83 µg PEGDGE) on the concentration of biotinylated peroxidase (B-POD) in the solution. There was a 25 minute incubation between B-POD additions. Successive additions of B-HRP were made to an incubation solution containing 100 µM $H_2O_2$ in which the PVI-Os-avidin electrode was operated. The conditions were again 5 mL PBS, 1000 RPM, and 100 mV AgAgCl. After a concentration of 0.3 µg/mL B-HRP was reached, the current no longer increased, suggesting saturation of all the avidin binding sites. This concentration corresponds to 1.2 B-HRP molecules per avidin, i.e. occupation of only 30% of the four avidin binding sites, if the manufacturer's assay of one binding site per 20 kD for avidin and of one B-HRP molecule per 50 kD in the preparations is correct. If the assays are correct, then the data suggests that in the cross-linked gel about one third of the binding sites are accessible to the permeating B-POD within the 25 min. incubation period between successive additions of B-POD.

Figure 8:
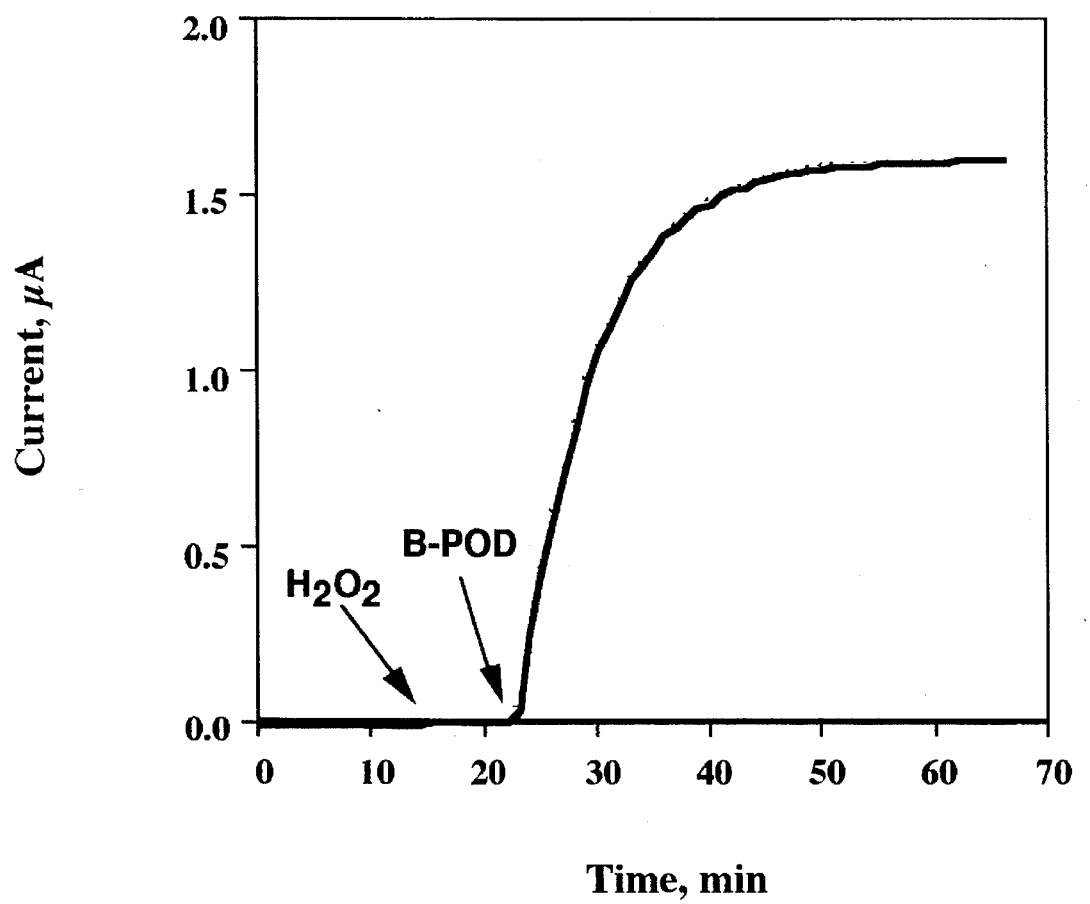

FIG. 8 shows the time dependence of the binding event and the current generated from a PVI-Os avidin modified electrode (3.3 µg PVI-Os, 2.0 µg avidin, and 0.83 µg PEGDGE) after injecting $H_2O_2$ to 100 µM an injecting B-POD to 1 µg/ml concentration. The conditions were as in FIGS. 6 and 7. FIG. 8 shows that the current increases to half of its final value in less than 5 min. and to 90% of its final value in less than 15 min. when the PVI-Os-avidin modified electrode is incubated in a solution with 100 µM $H_2O_2$ and 1 µg/mL B-POD. In this experiment the immobilized avidin to solution B-HRP ratio was such that when 30% of all avidin sites in the film were occupied, 30% of the B-HRP was depleted from the solution. Because only 30% of all avidin sites in the film were accessible, the rapid initial increase in current followed by the slow increase is interpreted as resulting from rapid saturation of the easily accessible avidin binding sites, followed by slow reaction of B-HRP with the sites that are difficult to reach.

Non-specific binding of HRP to the, PVI-Os-32 wt. % avidin electrode produces an $H_2O_2$ electroreduction current, but this current is twelve fold smaller than the current resulting, at equal enzyme activity, from incubation with B-HRP. When B-HRP solutions were incubated with PVI-Os electrodes without avidin and with 32 wt. % avidin in the films, the respective ratio of currents was 1:12. We note,, nevertheless, that the non specific B-HRP adsorption characteristics of the surface could have also been affected by the presence of avidin. When the avidin in the films was replaced by BSA, the current after incubation with B-HRP was only 1/20th of that measured with avidin containing electrodes. Apparently, the positively charged PVI-Os surface and possibly avidin adsorbed non-specifically HRP, the isoelectric point of which is near 7.4. Incorporation of BSA reduced the electrostatic interaction and thus the non-specific adsorption.

EXAMPLE 3

Figure 9:
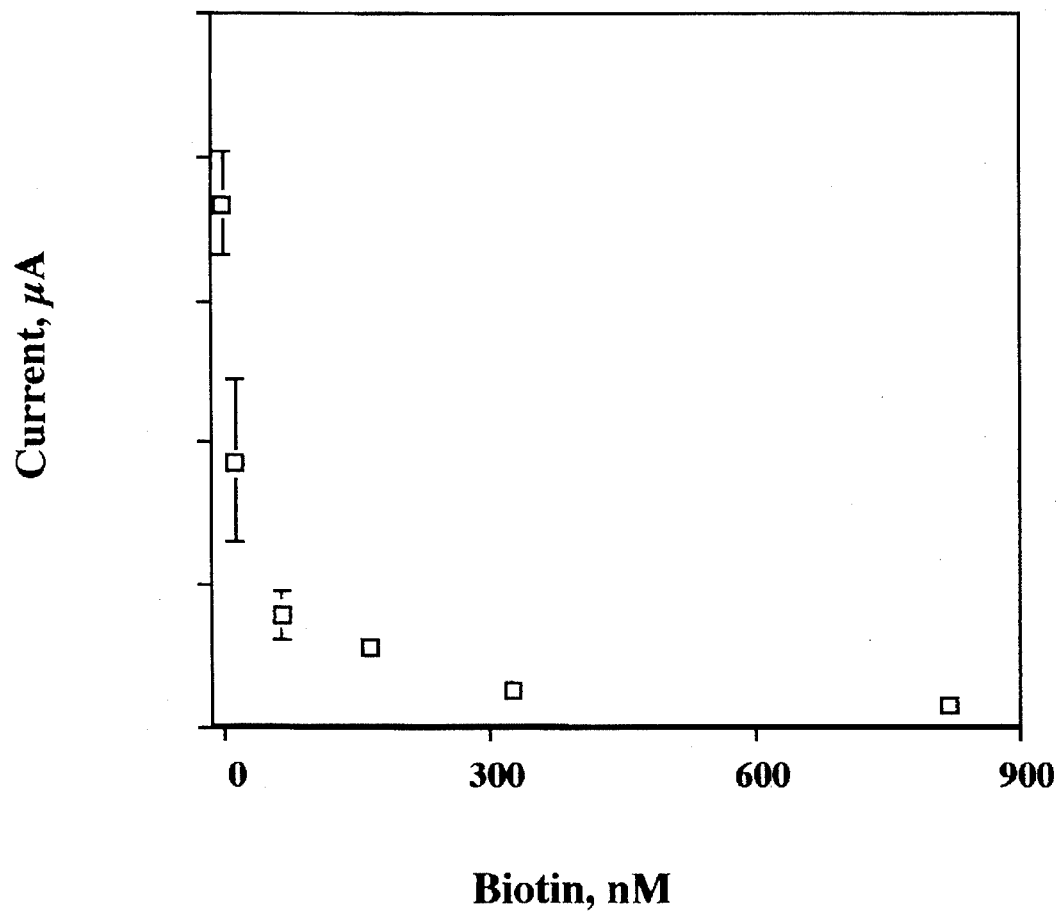

Operation of Avidin Affinity Electrodes in a Competitive Assay for Biotin or Avidin Electrode sensors were prepared as in example 1 and operated as in example 2. When the PVI-Os 32 wt. % avidin electrode was incubated in a solution of 300 µg/mL biotin for 25 min. prior to incubation with B-HRP (for a further 20 min.), the current was tenfold smaller than that seen without biotin preincubation. Beyond providing information on specificity, the experiment also showed that the avidin electrode can be used for assaying biotin in the solution. FIG. 9 shows the dependence of the current on the biotin concentration in the solution in which the PVI-Os-avidin electrode was preincubated for 20 minutes. Error bars represent the standard deviation for 3 or 4 tests. The conditions were 5 mL PBS, 1000 RPM, and 100 mV AgAgCl.

Figure 10:
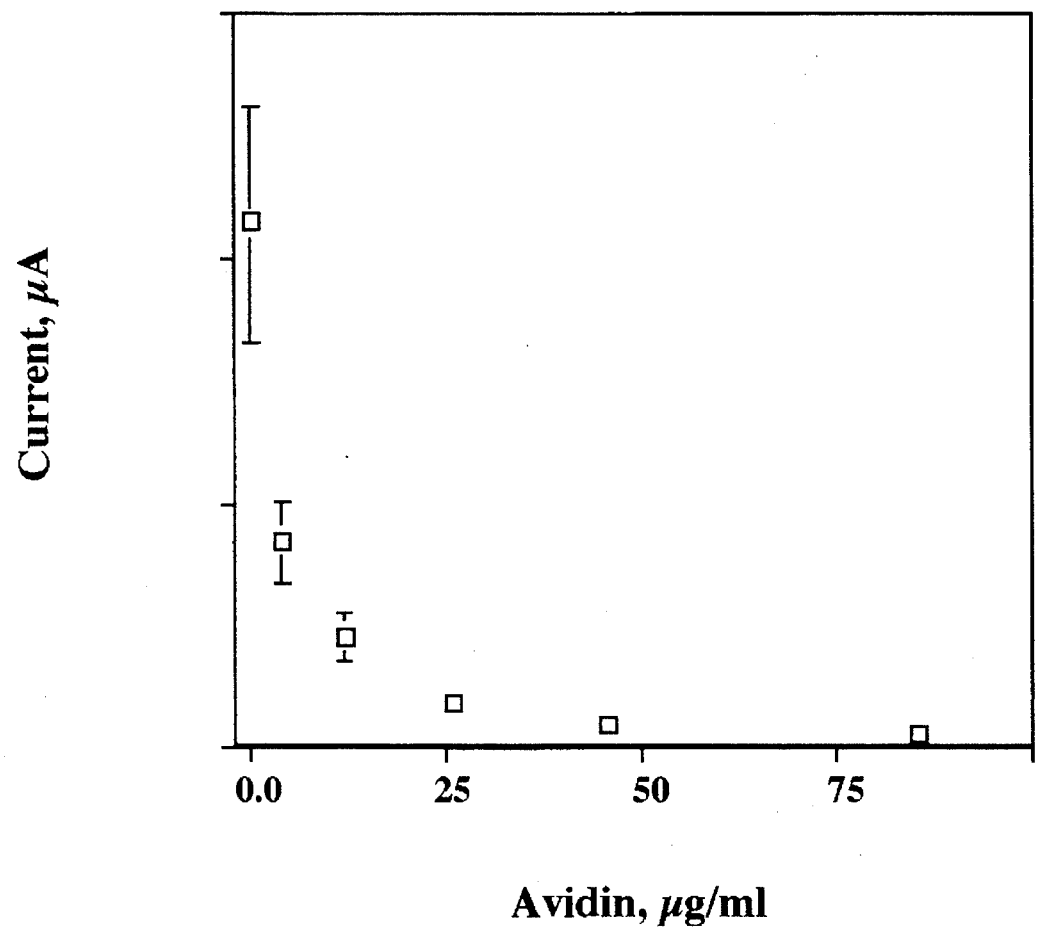

In a similar manner, when an excess of avidin was added to the B-HRP solution prior to incubation with the PVI-Os 32 wt. % avidin electrode, i.e. when an excess of dissolved avidin competed for the dissolved B-HRP, the current decreased practically to nil. FIG. 10 shows the dependence of the electrocatalytic $H_2O_2$ reduction current on the avidin concentrations in 1 µg/ml B-POD solutions in which the PVI-Os-avidin electrodes were incubated for 20 minutes. B-POD was added to a solution already containing the avidin and stirred with the PVI-Os-avidin coated electrode. The dissolved B-POD and avidin were not preincubated. Error bars represent the standard deviation for 3 or 4 points. Conditions are the same as FIG. 9. Again, beyond providing information on specificity, the experiment shows that the electrode can be used to assay dissolved avidin in a solution. The presence of 4 µg/mL of avidin in the solution lowered the current from 1 µA to 0.4 µA. Considering that a 0.1 µA change can be reproducibly measured, the experiment showed that 1 µg/mL of avidin can be readily assayed.

EXAMPLE 4

Production of an Antibiotin Containing ,Affinity Electrode

Glassy carbon electrodes were made and polished as in example 1. Goat antibiotin was obtained from Pierce (product number 31852) as a freeze-dried powder. The electrodes were coated with 1 µL of a solution containg 2.5 µg/ml PEGDGE, 1 mg/ml goat antibiotin, and 10 mg/ml PVI-OS mixed in a 1:5:1 ratio (PEGDGF:antibiotin:PVI-Os).

EXAMPLE 5

Operation of Antibiotic Affinity Electrodes

Figure 11:
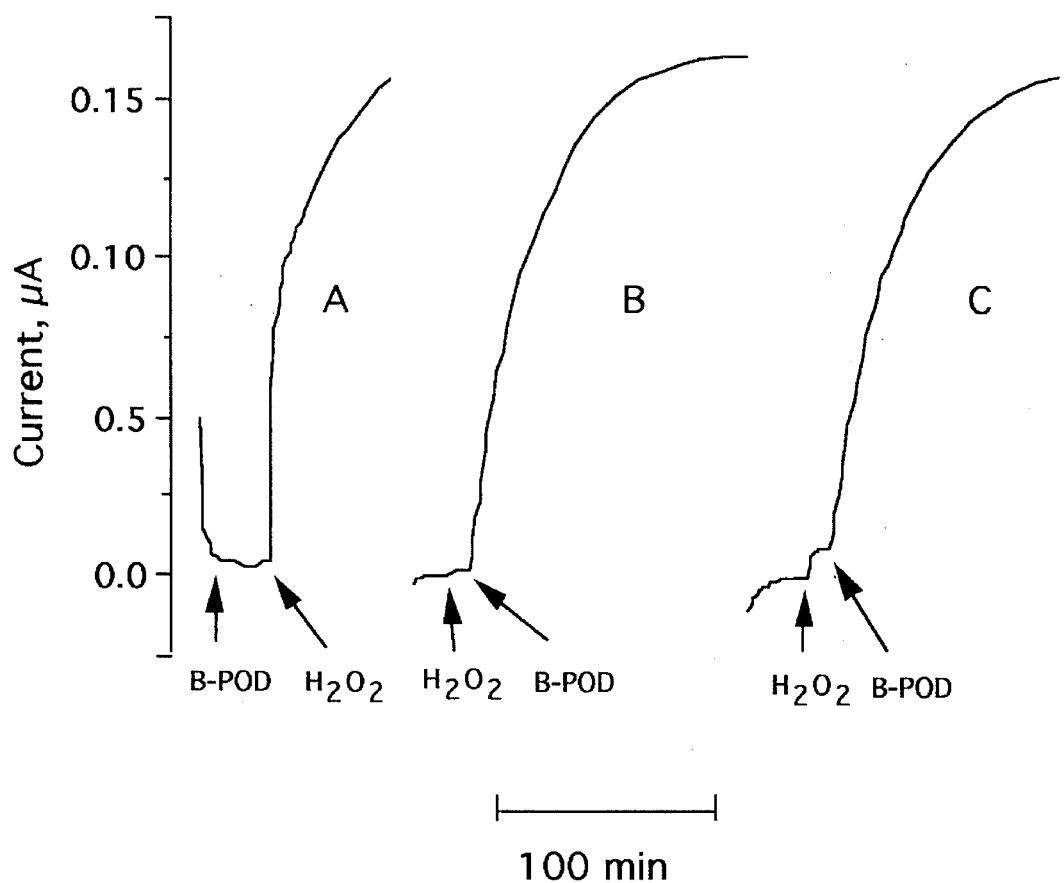

These affinity electrodes are manufactured as in example 4 and operated as in example 2. As yet, a wash solution has not been found that effectively separates biotin from avidin without destroying the ability of avidin to bind biotin, or change the redox characteristics of the PVI-Os films. This is not unexpected considering that the couple does not separate even at extremes in pH.[3] The lack of reversibility makes it necessary to use multiple electrodes in establishing calibration curves (FIGS. 9 and 10). Work with antibiotin antibody immobilized in PVI-Os gels on electrodes has shown, that as with the PVI-Os-Avidin films, the binding of B-HRP can be tracked by the increase of $H_2O_2$ reduction current. However, unlike the PVI-Os-avidin film, where binding was practically irreversible, the B-HRP bound reversibly to the antibiotin containing film. In three cycles of binding and separation the current increased and decreased reproducibly, showing that the film did not degrade upon brief cycling. FIG. 11 shows three biotin labeled peroxidase binding cycles (A, B, and C) for the immunosensor described in example 4. The B-POD binding event was carried out in 5 μL pH 7.4 PBS. The $H_2O_2$ concentration was 0.1 μM and the B-POD concentration was 1 μg/mL. The electrode was rotated at 1000 rpm and poised at 100 mV vs. Ag/AgCl. The binding was reversed by washing the electrode in pH 2 PBS for 2 hours.

[3] Green, N. M. In *Adv. in Protein Chemistry*, Anfinsen, C. B.; Edsall, J. T.; Richards, F. M., Ed.; Academic Press: New York, 1975; Vol. 29; p. 85–133.

CONCLUSION, RAMIFICATIONS, AND SCOPE

The work describes principles for direct electrical detection of the occurrence of an affinity reaction. The sensitivity and detection limits are adequate for some of the widely performed assays. The microampere currents measured were one thousand fold higher than those routinely measured with simple and inexpensive ($200) potentiostats. They were a million fold higher than currents measured in Faraday cages with state of the art low noise current amplifiers and potentiostats. Considering that in the experiments all the affinity reagent was stripped from a large 5 mL volume, no obstacle can be seen to detecting thousand and even million fold smaller amounts of affinity reagents, simply by using smaller electrodes. For example, by using standard 1–10 μm diameter microelectrodes, the sensitivity could be increased by a factor of $10^5$. Another area where progress can be expected is making affinity sensors for multiple assays. The strong bond of the avidin-biotin makes the electrodes described in examples 1, 2 and 3 practically irreversible. Examples 4 and 5 show electron conducting films of hydrogels with reversibly binding affinity reagents are possible. In all of these the assays could be accomplish without washing of the electrodes.

We claim that:

1. An electrode for the detection or quantification of a Selective Binding reaction comprising: an electrode having a testing surface substantially covered with a transducing film comprising an immobilized polymer network which provides for electrical conduction in the absence of diffusional mediators and a selective binding unit (SBU) where the SBU where the SBU has a specific affinity for a chemical, biological agent, or a class of chemicals, and includes immobilizing and oxidoreductase to the SBU's conjugate to bind with the SBU, wherein the oxidoreductase is reversibly immobilized at the electrode and electrical conduction between the electrode and the immobilized oxidoreductase occurs.

2. The electrode of claim 1, wherein the immobilizing polymer is a redox polymer containing osmium based redox centers.

3. The electrode of claim 1, wherein the immobilizing polymer is poly(vinyl pyridine) complexed with osmium bis (2,2'-bipyridine) dichloride.

4. The electrode of claim 1, wherein the immobilizing polymer is poly (N-vinyl imidazole) complexed with osmium bis(2,2'-bipyridine) dichloride.

5. The electrode of claim 1 where the selective binding unlit is Avidin or streptavidin.

6. The electrode of claim 1 where the selective binding unit is an antibody.

7. The electrode of claim 1 where the selective binding unit is a lectin, specific sugar residue, or single strand of DNA.

8. A method for sensing the occurrence of a binding reaction between a selective binding unit (SBU) and a conjugate to the SBU where changing of the incubation solution is not necessary to differentiate bound and unbound conjugate comprising the steps of coating a current collecting electrode with a hydrogel, the polymer network of which comprises SBUs and multiple reducible and oxidizable centers chemically bound to the network, immersing the hydrogel coated electrode in a solution containing the conjugate, to which an oxidoreductase is covalently bound, allowing the SBU to bind with its conjugate, and measuring the current frown the electrode when the electrolytic solution contains a substrate of the oxidoreductases.

9. A method as in claim 8 where the oxidoreductase label is a peroxidase.

10. A method as in claim 8 where the selective binding occurs between an antigen and an antibody, DNA complimentary strands, or lectin and specific sugar residues.

11. A method as in claim 8 where the selective binding occurs between biotin and avidin.

12. A method as in claim 8 where the selective binding occurs between biotin and an antibody to biotin.

13. A method as in claim 8 where an analyte is detected or quantifies by the analytes competition with a labeled complement for limited binding sites at the affinity electrode.

14. A method as in claim 8 where an analyte is detected or quantified by the analytes binding oxidoreductase labeled complement thus preventing the labeled complement from binding with selective binding units immobilized at the sensor surface.

15. A method as in claim 8 where the modified electrode uses an osmium redox polymer to supply the oxidizable/reducible species.

* * * * *